(12) United States Patent
Harter

(10) Patent No.: US 6,971,877 B2
(45) Date of Patent: *Dec. 6, 2005

(54) DENTAL IMPLANT TOOL WITH ATTACHMENT FEATURE

(75) Inventor: Robert J. Harter, La Crosse, WI (US)

(73) Assignee: Leo J. Malin, La Crosse, WI (US)

( * ) Notice: Subject to any disclaimer, the term of this patent is extended or adjusted under 35 U.S.C. 154(b) by 165 days.

This patent is subject to a terminal disclaimer.

(21) Appl. No.: 10/429,085

(22) Filed: May 2, 2003

(65) Prior Publication Data
US 2004/0219478 A1 Nov. 4, 2004

(51) Int. Cl.$^7$ ................................................ A61C 3/00
(52) U.S. Cl. ......................................................... 433/75
(58) Field of Search .............................. 433/75, 76, 72, 433/173, 174; 606/80, 96; 408/241 B, 241 G, 72 B, 115 R, 115 B; 33/638

(56) References Cited

U.S. PATENT DOCUMENTS

| | | | |
|---|---|---|---|
| 3,078,580 A | * | 2/1963 | Galvez .......................... 433/76 |
| 3,748,739 A | | 7/1973 | Thibert |
| 4,998,881 A | | 3/1991 | Lauks |
| 5,015,183 A | | 5/1991 | Fenick |
| 5,015,186 A | | 5/1991 | Detsch |
| 5,064,374 A | | 11/1991 | Lundgren |
| 5,133,660 A | | 7/1992 | Fenick |
| 5,350,297 A | | 9/1994 | Cohen |
| 5,613,852 A | | 3/1997 | Bavitz |
| 5,718,579 A | | 2/1998 | Kennedy |
| 5,800,168 A | * | 9/1998 | Cascione et al. ............. 433/75 |
| 5,989,025 A | * | 11/1999 | Conley ......................... 433/76 |
| 6,283,753 B1 | | 9/2001 | Willoughby |
| RE37,646 E | | 4/2002 | Zuest |
| 6,488,502 B1 | | 12/2002 | Weber |
| 2002/0182567 A1 | | 12/2002 | Hurson et al. |
| 2003/0083667 A1 | * | 5/2003 | Ralph et al. ................... 606/96 |

FOREIGN PATENT DOCUMENTS

| | | |
|---|---|---|
| EP | 0437031 A1 | 7/1991 |
| WO | WO99/26540 | 6/1999 |

* cited by examiner

Primary Examiner—Melba N. Bumgarner
(74) Attorney, Agent, or Firm—Robert J. Harjer

(57) ABSTRACT

A dental tool for guiding a drill bit during a dental implant procedure includes a pivotal drill bushing attached to a bushing holder. The bushing holder, in turn, is attached to a surgical dental stent that fits a patient's jaw. The bushing holder attaches to the stent by extending into a hole or bore of the stent. In some cases, the bushing holder snaps into the hole.

7 Claims, 4 Drawing Sheets

DENTAL IMPLANT TOOL WITH ATTACHMENT FEATURE

BACKGROUND OF THE INVENTION

1. Field of the Invention

The subject invention generally pertains to dental implants and more specifically to a tool for installing them.

2. Description of Related Art

Various dental implant methods and devices have been developed for replacing one or more missing teeth in a person's jaw with prosthetic teeth. For many prosthetic teeth, a final product comprises three basic components: an implant, an abutment, and a crown. The crown is the exposed portion of the prosthesis that resembles one or more teeth. The implant is an anchor that becomes attached to the jawbone, and the abutment couples the crown to the implant.

To install the implant, a hole is usually drilled into the patient's jawbone, and the implant is inserted into the hole.

A drill bushing attached to a stent can be used to help guide the drill bit, as disclosed in PCT Publication WO 99/26540 and U.S. Pat. Nos. 5,015,183; 5,133,660; 5,718,579. A drill bushing, unfortunately, can be difficult to attach to a stent, particularly if the drill bushing is to be pivotal relative to the stent as is the case in the U.S. Pat. No. 5,718,579 patent.

Thus, a need exists for a pivotal drill bushing that includes a feature for allowing the bushing to be readily attached to a stent.

SUMMARY OF THE INVENTION

To attach a pivotal drill bushing to a surgical stent, it is an object of some embodiments of the invention to attach the drill bushing to a bushing holder and have the bushing holder extend into a bore of the stent.

Another object of some embodiments is to have the bushing holder engage the inside diameter of the bore.

Another object of some embodiments is to provide the bushing holder with a snap-in feature that allows the holder to snap into engagement with the stent.

Another object of some embodiments is to have the bushing holder engage the bore of the stent.

Another object of some embodiments is to provide the bushing holder with a flange that establishes the axial position of the holder relative to the stent.

Another object of some embodiments is to enable the drill bushing to pivot about two axes that lie at right angles to each other.

One or more of these and other objects of the invention are provided by a dental tool that includes a drill bushing pivotally attached to a bushing holder, wherein the bushing holder extends into a bore of the stent.

DESCRIPTION OF THE PREFERRED EMBODIMENT

Figure 1:
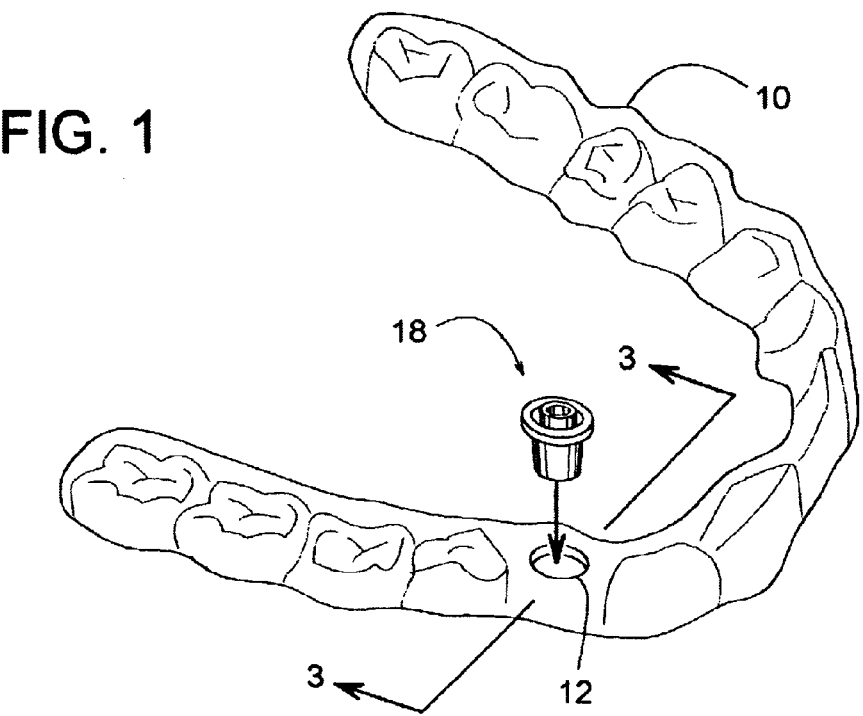
FIG. 1 is a perspective view showing a dental tool being inserted into a dental stent.
Figure 2:
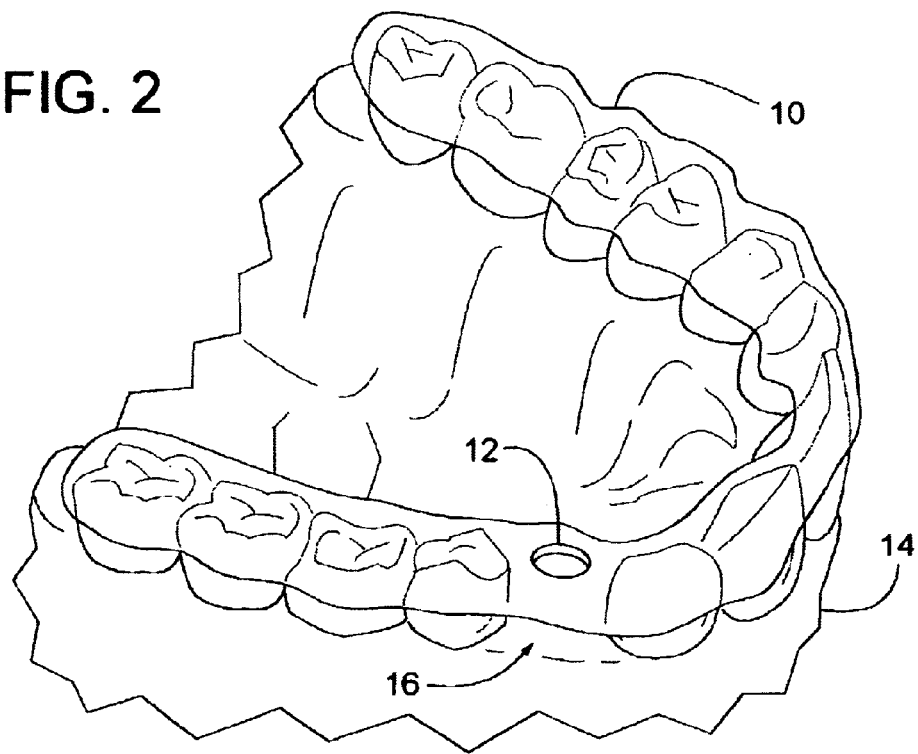
FIG. 2 is a perspective view showing the stent attached to a patient's upper or lower jaw.

FIG. 1 shows a dental stent 10 having a hole or bore 12, and FIG. 2 shows stent 10 attached to a patient's jaw 14 (upper or lower jaw). The term, "jaw" refers to that part of a patient's body that comprises one or more of the following: teeth, gums, and/or jawbone (upper or lower). Stent 10 is a conventional surgical dental stent that can be produced in various ways that are well known to those skilled in the art. Stent 10 can be hollow or solid in an area 16 of the missing tooth. Bore 12, which is in area 16 of the missing tooth, can be created in stent 10 by various methods including, but not limited to, drilling, punching, cutting, etc.

Figure 3:
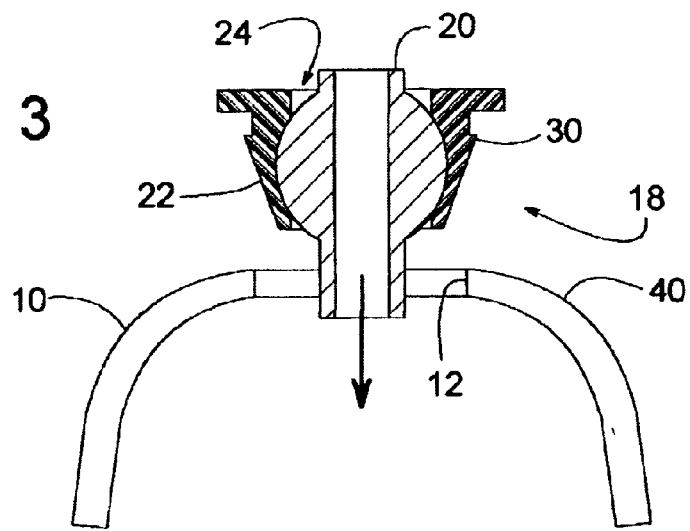
FIG. 3 is a cross-sectional view taken along line 3—3 of FIG. 1
Figure 7:
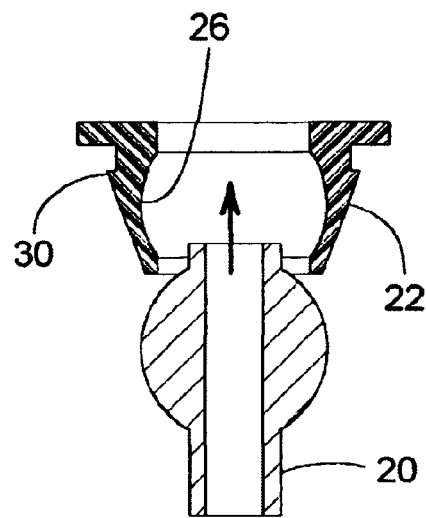
FIG. 7 is an exploded cross-sectional view of the dental tool of FIG. 3.

FIGS. 1 and 3 show a dental tool 18 being inserted into bore 12. Dental tool 18 comprises a drill bushing 20 attached to a bushing holder 22. A ball-and-socket joint 24 enables drill bushing 20 to pivot relative to bushing holder 22. More specifically, bushing 22 can pivot to set the angle of a drill bit's trajectory. To prevent bushing 20 from pivoting too freely within holder 22, an interference fit preferably exists between bushing 20 and holder 22. FIG. 7 shows drill bushing 20 being forced into a cavity 26 of holder 22.

Figure 4:
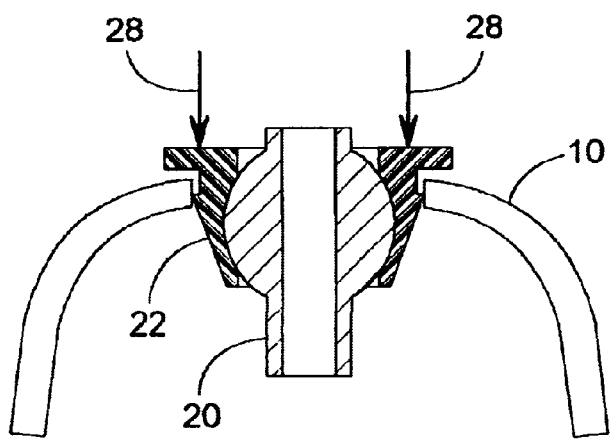
FIG. 4 is similar to FIG. 3, but showing the dental tool further into the stent.

Bushing holder 22 can be manually pushed into bore 12 as indicated by arrows 28 of FIG. 4. In some cases (but not all cases), holder 22 includes a snap-in mechanism 30 that helps hold bushing holder 22 in place within bore 12. In some cases, holder 22 can be held within bore 12 by way of a conventional bonding material or an interference fit between holder 22 and bore 12. The term, "snap-in" refers to the mating of two parts where at least one of the parts (e.g., holder 22 and/or stent 10) deflects or experiences strain during the engagement process (FIG. 4), and that deflection or strain diminishes upon completion of the engagement (FIG. 5).

Figure 5:
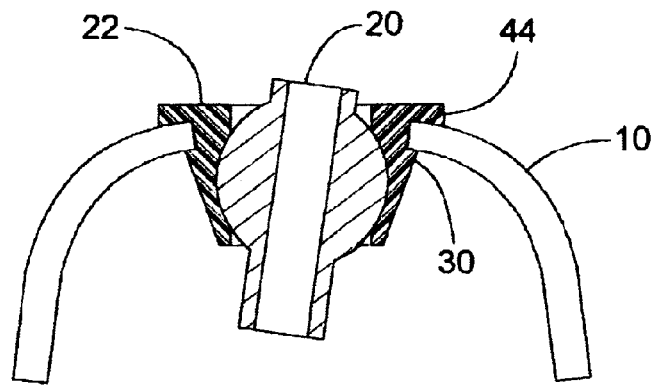
FIG. 5 is similar to FIG. 1 but showing the dental tool fully inserted and showing the pivoting ability of the drill bushing.
Figure 6:
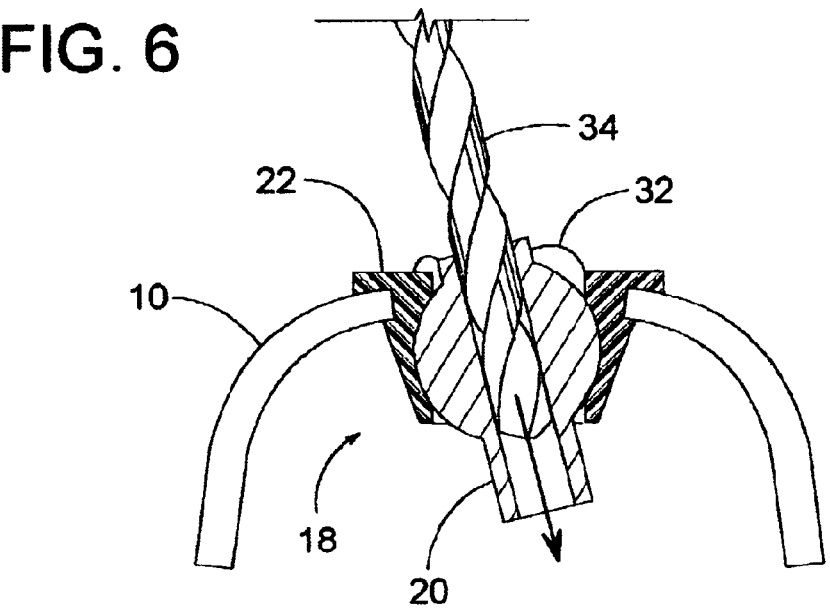
FIG. 6 is a cross-sectional view similar to FIG. 5 but showing a drill bit inserted into the dental tool.

FIG. 5 also shows the drill bushing's ability to pivot within holder 22, whereby drill bushing 20 can be aimed directly into the patient's jawbone. Once drill bushing 20 is properly oriented, as shown in FIG. 6, a conventional bonding material 32 can hold bushing 20 stationary relative to holder 22. In some case additional bonding material can help affix holder 22 to stent 10. With dental tool 18 being fixed relative to stent 10 and stent 10 being fixed relative to the patient's jaw 14, drill bushing 20 can help guide a drill bit 34 in drilling a hole into the patient's jawbone.

Figure 8:
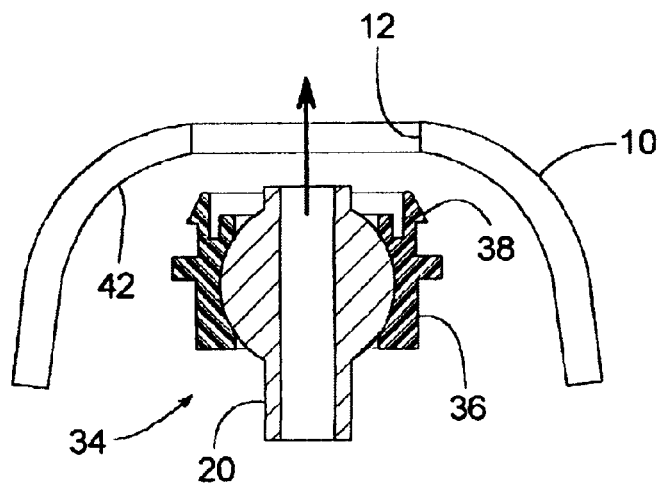
FIG. 8 is similar to FIG. 3 but showing another embodiment of a dental tool.
Figure 9:
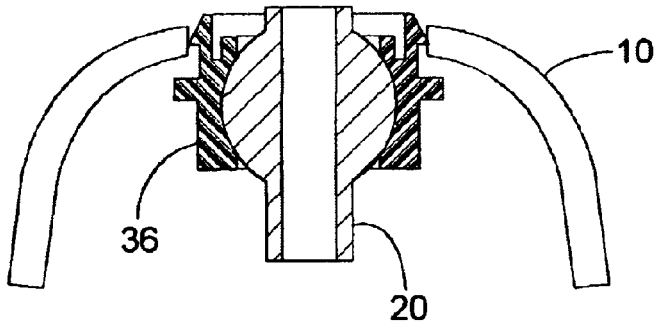
FIG. 9 is similar to FIG. 4 but showing the dental tool of FIG. 8.
Figure 10:
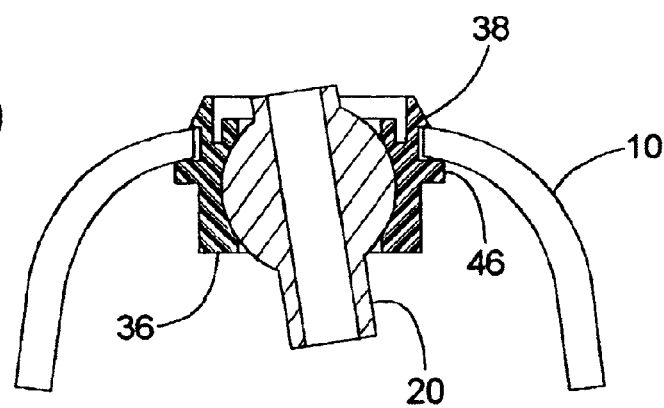
FIG. 10 is similar to FIG. 5 but showing the dental tool of FIG. 8.

FIGS. 8, 9, and 10 illustrate another dental tool 34 being inserted into bore 12 of stent 10. In this example, a bushing holder 36 includes a snap-in feature 38 that allows dental tool 34 to be inserted from another side of stent 10. In FIG. 3, tool 18 is shown being installed from a convex side 40 of stent 10. And in FIG. 8, tool 34 is shown being installed from a concave side 42 of stent 10.

In some cases, the bushing holder can be provided with a flange that helps establish the axial position of the dental tool. For example, holder 22 of FIG. 5 includes a flange 44, and holder 36 of FIG. 10 includes a flange 46. In both cases, the outer diameter of the flange is preferably larger than an inside diameter of bore 12. The flange may extend continuously around the bushing holder or may extend just partially around it. Thus, the term, "flange" broadly encompasses any radial extending protrusion, with the protrusion's "outer diameter" being twice the radial distance from a longitudinal centerline of the drill bushing to a radial extremity of the protrusion.

In some cases, the bushing holder engages the inside diameter of the bore (e.g., holder 22 engages bore 12), and in other cases, the bushing holder does not engage the inside diameter of the bore (e.g., a small radial clearance exists between holder 36 and bore 12).

Although the invention is described with reference to a preferred embodiment, it should be appreciated by those skilled in the art that various modifications are well within the scope of the invention. Therefore, the scope of the invention is to be determined by reference to the claims that follow.

I claim:

1. A dental tool for guiding a drill bit relative to a jaw of a patient, the dental tool comprising:
   a stent defining a bore therethrough and being adapted to fit and engage the jaw;
   a bushing holder extending into the bore of the stent, wherein the bushing holder includes a snap-in mechanism that connects the bushing holder to the stent; and
   a drill bushing adapted to receive the drill bit and being pivotally attached to the bushing holder.

2. The dental tool of claim 1, wherein the bushing holder includes a flange extending radially therefrom, wherein the flange engages the stent.

3. The dental tool of claim 1, wherein the bushing holder includes a flange extending therefrom, wherein the flange engages the stent and has an outer diameter that is greater than an inner diameter of the bore.

4. The dental tool of claim 1, wherein the bushing holder and the drill bushing creates a ball-and-socket joint therebetween.

5. The dental tool of claim 1, wherein the ball-and-socket joint provides an interference fit between the drill bushing and the bushing holder.

6. A dental tool for guiding a drill bit relative to a jaw of a patient, the dental tool comprising:
   a stent defining a bore therethrough and being adapted to fit and engage the jaw;
   a bushing holder extending into the bore of the stent, wherein an interference fit exists between the bushing holder and the bore to help hold the bushing holder to the stent; and
   a drill bushing adapted to receive the drill bit and being pivotally attached to the bushing holder.

7. The dental tool of claim 6, further comprising a flange extending radially outward from the bushing holder and being adapted to engage the stent.

* * * * *